United States Patent
Daxer

[19]

[11] Patent Number: 5,938,620
[45] Date of Patent: Aug. 17, 1999

[54] APPARATUS FOR TESTING COLOR DISCRIMINATION IN THE HUMAN VISUAL SYSTEM

[76] Inventor: Albert Daxer, Rotenmühlgasse 16/13, 1120 Wien, Austria

[21] Appl. No.: 08/868,979

[22] Filed: Jun. 4, 1997

[30] Foreign Application Priority Data

Jun. 5, 1996 [AT] Austria ......................................... 466/97

[51] Int. Cl.$^6$ ......................................................... A61B 3/02
[52] U.S. Cl. .............................................................. 600/558
[58] Field of Search ............................ 600/558; 399/227, 399/222, 264, 276, 38, 39, 40, 41

[56] References Cited

U.S. PATENT DOCUMENTS

| | | | |
|---|---|---|---|
| 4,697,915 | 10/1987 | Hayashi et al. | 399/227 |
| 5,280,323 | 1/1994 | Alvarez et al. | 399/264 |

FOREIGN PATENT DOCUMENTS

| | | |
|---|---|---|
| 59-116046 | 4/1984 | Japan . |
| 2192079 | 12/1987 | United Kingdom . |
| WO 88/03776 | 6/1988 | WIPO . |

OTHER PUBLICATIONS

Donaldson, G.B., *Instrumentation for the Farnsworth–Munsell 100–hue test\**, JOSA Letters, pp. 248–249, 1977.
Schnelder, T., *Einführung in die Farbsinnprüfung*, Augenärztliche Untersuchungsmethoden, pp. 29–35, 1989.

*Primary Examiner*—George Manuel
*Attorney, Agent, or Firm*—Brinks Hofer Gilson & Lione

[57] ABSTRACT

The present invention is directed to an automated determination of the sequence of color caps in a color spot or color arrangement test, such as Farnsworth-Munsell 100-Hue Test for determining the color discrimination of human beings. To that end, on or in the color caps, locations (sites) are fixed, at which magnets can be mounted. The distribution of magnets and voids (absence of magnets) are different for each color cap, among the fixed locations in the color caps and thus encode the color caps. A different type of encoding can be attained by creating variously strong magnetic fields by use of various strength magnets in the color cap. Magnetic field detectors are mounted at suitable points in the surface in which the color caps rest in the tray. Using these magnetic field detectors and corresponding electronics, the sequence of the color caps is determined. By means of a symmetry-breaking structure on the color caps or by suitable magnets of different strength on or in the color caps, a reliable evaluation secure against rotation of color caps is made possible.

7 Claims, 1 Drawing Sheet

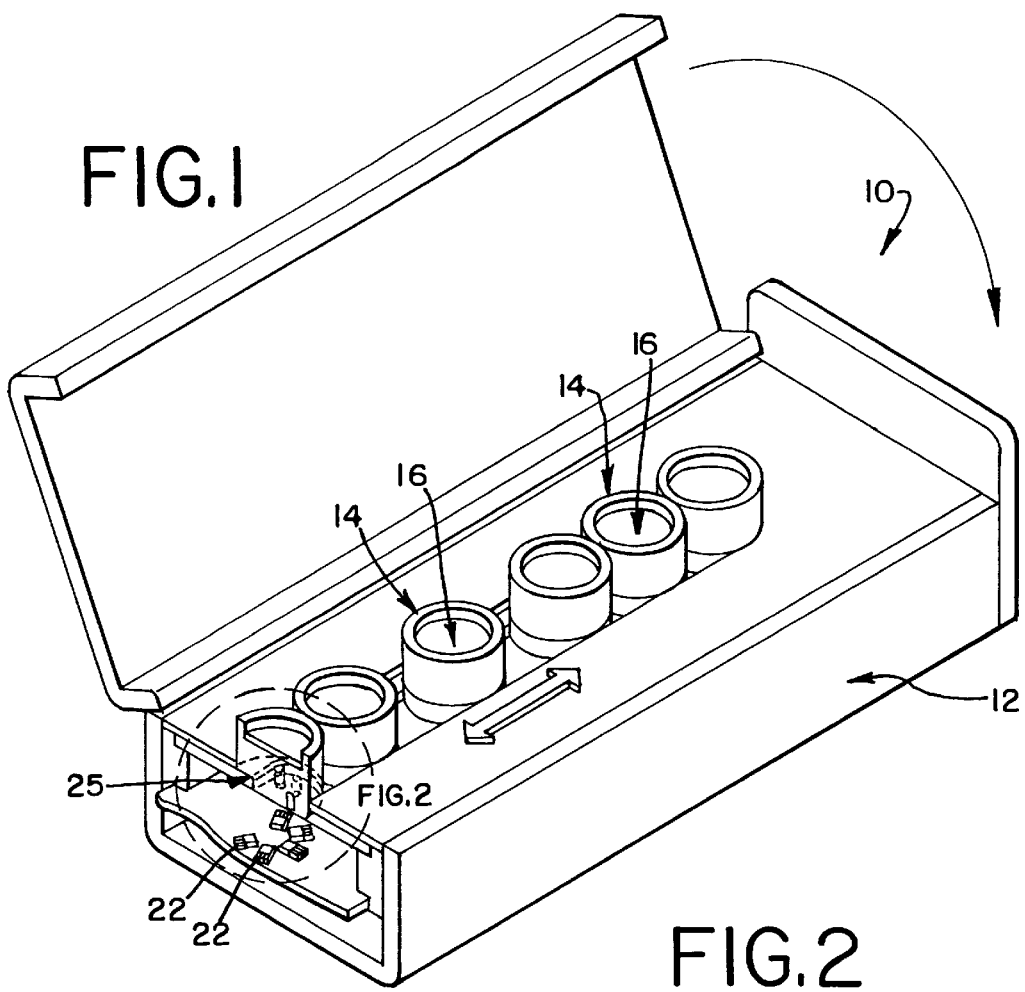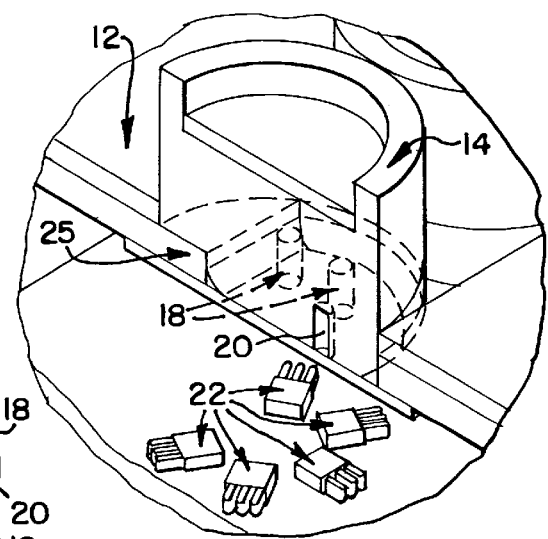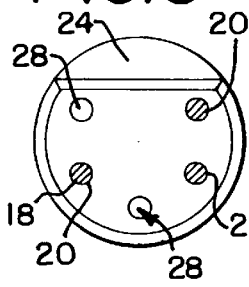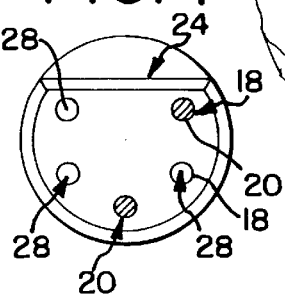

APPARATUS FOR TESTING COLOR DISCRIMINATION IN THE HUMAN VISUAL SYSTEM

The present invention is directed to an apparatus for testing color discrimination in the human visual system, and more particularly, an apparatus for automatically detecting the sequence of color caps in color spot or color arrangement tests such as the Farnsworth-Munsell 100-Hue Test.

BACKGROUND OF THE INVENTION

There are various methods for ascertaining the color discrimination of human beings. One known method is the color spot or color arrangement test. T. Schneider describes such a method in an article entitled "Einführung in die Farbsinnprüfung," (Introduction to Color Discrimination Testing) Z. Prakt. Augenheilkd (Journal for Practical Ophthamology), vol. 10, pp. 29–35 (1989). The principle of this test is to present the subject with a series of various color spots and ask the subject to arrange the spots in the correct sequence in accordance with the gradual color change. For those whose color vision is impeded, mistakes that are more or less characteristic for the particular disorder occur.

The best known example of this type of color vision test is the Farnsworth-Munsell 100-Hue Test which has 85 movable and 8 fixed color caps each with a diameter of 5 mm. Taken together, these 93 caps form a sample of the natural color spectrum and of the range of purple colors. The caps are distributed among four trays. When placed one abutting the other using the criterion that the most similar colors are arranged one after the other, the caps produce a closed color circle. Each cap and hence each color spot is assigned a number which makes it possible to calculate how many partial mistakes are made and to calculate the total number of mistakes. The total number of mistakes, particularly in inherited color vision disorders, is a good parameter for monitoring the course of any disorder.

Ascertaining the number of mistakes is relatively time-consuming, however, and involves a certain likelihood of error. Attempts have been made to reduce the effort by using suitable computer programs but the sequence in which the subject places the cap cannot be used to calculate the numbers of mistakes until after it has been entered manually into the computer. Although this does accomplish a certain time savings in calculation, nevertheless the input itself is time-consuming as well, and above all requires high concentration if data entry errors are to be kept low.

Other methods utilize automated systems. G. B. Donaldson describes in article entitled "Instrumentation for the Farnsworth-Munsell 100-Hue Test," J. Opt. Soc. Am., vol. 67, pp. 248–9 (1977), an apparatus for automated ascertainment of the sequence of color spot disks. Switch elements in the form of one resistor and one Zener diode are each mounted and connected in parallel in the caps that contain the color disks. By suitable combinations of these switch elements, it is possible to encode the color disks suitably and by using electrical plug connections mounted on the underside of the color caps the sequence in which the color disks are placed can be ascertained. Several disadvantages are associated with this method. In order to perform the method, the subject (patient) needs to rearrange the color caps, which are usually in random order, in front of the subject (patient) on a table top. In the normal Farnsworth-Munsell 100-Hue Test this does not create a problem since the underside of each cap is flat. In the automated version described by Donaldson, simply placing the randomly ordered color caps on the table top is not possible because the color caps do not have a flat bottom surface, and thus the individual color caps can no longer be placed on the table in front of the subject stably with the colored surface facing upward. Instead, because the color caps have a plug mounted on their underside the color caps rest somewhat like a toy top on the flat surface of the table and the colored surfaces of the caps are oriented in an arbitrary direction instead of facing upward toward the subject. This hinders the subject's ability to make a color choice. Also, the color spot disks should be displaceable in the arrangement direction so that if the subject wants to place one more color caps between two or more color caps that have already been put in place, the subject can create a suitable space by shifting the already-placed caps. This is not possible in Donaldson's automated method because all of the caps that are already arranged have to be unplugged from the plug connections and plugged into the positions corresponding to the necessary shifting. Only then can the subject plug the desired cap into the position that has now been made available. If the subject, once he has looked at the partial color sequence thus arranged decides that the cap now placed in between other color caps still does not fit this location in terms of its color, which is often the case, then the subject has to undo all the unplugging and plugging maneuvers he has already performed. In addition, the plug connection is not only an electrical part but also a mechanical part and is thus vulnerable to wear. Also the electrical components of the color caps have a relatively limited service life. If the Zener diode in the interior of the color cap should break, for instance, it must be replaced which would involve a not inconsiderable amount of effort.

To circumvent at least some of these disadvantages, PCT Application No. WO 88/0317A1 published Jun. 2, 1988 describes an apparatus for automated determination of the color sequence arranged in color arrangement tests. More particularly, a bar code-type reader system is employed. A bar code, preferably formed by concentric rings, is placed on each of the color caps so that each color cap, regardless of its orientation can be identified using a scanner. There are several disadvantages associated with this method. Because a suitable scanner must scan across the color caps, a movable mechanical device is required. This introduces a certain vulnerability in the system to malfunction and a certain need for repair and maintenance which increases with the more tests per unit of time that are performed. Also, the mechanical system must be of high quality and is therefore expensive. In addition, bar code systems are not immune from error, not every attempt at reading is successful. Also, the scanner device can become dirty which leads to an increased need for maintenance.

Thus it is desirable to provide an apparatus for the automated determination of the sequence of color caps in a color spot or color arrangement test that does not have the disadvantages listed above.

SUMMARY OF THE INVENTION

According to a first aspect of the present invention there is provided an apparatus for determining the color discrimination of a subject including a positioning tray, a plurality of color caps movably located in the positioning tray and at least one magnet located on at least one of the plurality of color caps.

BRIEF DESCRIPTION OF THE DRAWINGS

FIG. 1 is a perspective view of an apparatus used to carry out the automated determination of the sequence of color caps.

FIG. 2 is an exploded view of a portion of the positioning tray and a color cap shown in FIG. 1.

FIGS. 3 and 4 illustrate the underside of two different color caps.

DETAILED DESCRIPTION OF THE PRESENTLY PREFERRED EMBODIMENTS

FIG. 1 is a perspective view of an apparatus 10 used to carry out the automated determination of the sequence of color caps. The apparatus 10 includes a positioning tray 12 which holds a plurality of color caps 14. In a preferred embodiment each color cap 14 has a color spot 16 located on the top side of the color cap 14 so that it is visible to the subject undergoing evaluation. The color caps are slidable in the direction shown by the double headed arrow to allow the subject to simply rearrange the sequence of color caps 14 according to their color as the subject undergoes evaluation.

FIG. 2 is an exploded view of a portion of the positioning tray 12 and a color cap 14 shown in FIG. 1. The underside of each color cap 14 has defined locations 18 which are shown in phantom. A magnet 20 may be positioned at a defined location 18. For example, in the preferred embodiment shown in FIGS. 1 and 2 the defined locations 18 are cylindrical holes formed in the underside of each cap 14 and the magnet 20 is cylindrical and fits inside the hole formed at a defined location 18. Of course the defined locations 18 and magnet 20 may have other embodiments and the present invention is not limited to those illustrated. The positioning tray 12 has a plurality of magnetic field detectors 22 underlying the defined locations 18 on the underside of the color caps 14. In a preferred embodiment the magnetic field detectors 22 are Hall detectors.

In a preferred embodiment the color caps 14 have a geometrical alteration, preferably a step 24, that breaks the symmetry of the underside of the color caps 14 and assures that the color caps will be oriented in such a way that the potential magnet positions, i.e., defined locations 18, in the color cap will come to rest above the corresponding magnetic field detector positions 22 when the color caps 14 are placed in the tray 12. More particularly, the step 24 rests on a ledge 25 formed in the positioning tray 12. In order to encode each color cap 14 the distribution of magnets 20 and voids (absence of magnets) at the defined locations 18 on the underside of a color cap 12 differs for each color cap.

FIGS. 3 and 4 illustrate the underside of two different color caps. The black circles 20 represent a magnet located at a defined location 18, and the white circles 28 represent a void or absence of a magnet at a defined location. The magnetic field detectors 22 located in the tray at locations corresponding to the defined locations on the underside of the color cap make it possible to determine which of the defined locations in the color cap have a magnet and which do not. This information is then processed by suitable electronics (not shown) such as an evaluation unit connected to the magnetic field detectors 22 and is preferably transmitted for further evaluation to a computer system (not shown). The step 24 formed on the underside of each cap 14 enables the positioning of the defined locations in the color caps above the corresponding locations for the magnetic field detectors 22 in the tray 12 and prevents the rotation of the color caps 14. Alternatively, in the coding of the color caps using several magnets, at least one magnet may be provided which serves for determining the orientation of the color cap. This magnet may be a component of the coding itself or it may be an additional magnet which forms no part of the coding. This magnet is distinguished from the other magnets by either the strength of the magnetic field it generates or the direction of its magnetic field compared with the other magnets. The position of this magnet with respect to the other magnets can be recognized by the magnetic detectors from which the alignment or orientation of the color cap may also be detected. Using such a magnet there is detected the beginning of the coding, i.e. first bit of a code word. In addition, the rotation of the color cap is not hampered and it is not necessary to position the color cap in the positioning tray in a defined orientation. Providing a symmetry breaking feature such as a step or bevel on the bottom of the color cap is no longer necessary.

Thus, the magnetic field coding of the color caps is detected by the magnetic field detectors and thereby each of the color caps is identified. On the basis of this identification a computer system determines the sequence of the color caps. In a manner not shown, a combination of the two embodiments is possible where the color caps are encoded by both the arrangement of the magnets and their strength. In addition, it is also possible to utilize the direction of the magnetic field created by a magnet or magnets to determine the color cap's orientation.

Compared with the known systems previously described, the present invention provides the following advantages. No mechanically movable parts or devices are necessary. In addition, the transmission of information between the color caps and the electronics in the tray takes place without electrical or mechanical contacts. The color caps contain no electronic or mechanical or optical components that are subject to wear thereby eliminating maintenance problems. Also, the color caps are easily shiftable in the tray (as long as not all the color caps have been put in place) and despite the symmetry-breaking alteration which in a preferred embodiment is a step on the underside of the color cap, the color caps can be positioned stably on a flat surface. This allows for ease of manipulation for patient and the professional performing the examination. Also, the design and the corresponding components of the apparatus 10 are comparatively inexpensive. Also, the system is extremely low power consumption since the color caps do not require a power supply.

In a second preferred embodiment a magnet or magnet system is mounted preferably at the geometric center of the color caps which encodes the individual color cap by the intensity of the magnetic field generated by the magnet and detected by the magnetic field detector positioned in the tray. The information about the magnetic field intensity prevailing at a particular color cap position in the tray is evaluated by an evaluation unit and may be displayed. This second preferred embodiment makes it possible to identify the color caps regardless of the cap's rotation and thus the caps do not require symmetry-breaking alterations, i.e., steps or bevels, for example. Thus the information about the particular color cap is encoded not by the arrangement of magnets on the underside of the color cap but rather by the intensity of the magnetic field generated by the magnets in the color cap.

It is to be understood that the forms of the invention as described herewith are to be taken as preferred examples and that various changes in the shape, size and arrangement of parts may be resorted to, without departing from the spirit of the invention or scope of the claims.

What is claimed is:

1. An apparatus for determining the color discrimination of a human being, the apparatus comprising:

a positioning tray;

a plurality of color caps movably located in the positioning tray;

at least one magnet located on more than one of the plurality of color caps wherein the position of the at least one magnet is related to the color of more than one of the plurality of color caps on which it is located; and a plurality of magnetic field detectors located in the positioning tray wherein the detectors are positioned to detect the at least one magnet of a color cap thereby indicating the position of the magnet in the color cap and the position of the at least one color cap in the positioning tray.

2. An apparatus according to claim 1 wherein more than one defined locations are located on each of the color caps and the at least one magnet may be positioned at at least one defined location wherein the position of the at least one magnet encodes the color cap.

3. An apparatus according to claim 2 wherein the detectors are located in the tray in positions that are aligned with the defined locations on the color caps.

4. An apparatus according to claim 1 wherein each color cap has a plurality of defined locations in which a magnet may be mounted wherein each color cap is encoded by mounting magnets at some of the defined locations and leaving other defined locations void of a magnet.

5. An apparatus according to claim 1 wherein the color caps have a step or bevel which corresponds to a ledge formed in the positioning tray so that when the color caps are positioned in the positioning tray, the step or bevel is aligned with the ledge.

6. An apparatus for determining the color discrimination of a human being, the apparatus comprising:

a positioning tray;

a plurality of color caps movably located in the positioning tray;

at least one magnet located on at least one of the plurality of color caps wherein the intensity of the at least one magnet is related to the color of the at least one of the plurality of color caps on which it is located; and at least one magnetic field detector located in the positioning tray wherein the at least one detector is positioned to detect the at least one magnet when the magnet is disposed over the detector thereby indicating the intensity of the magnet in the color cap and the position of the at least one color cap in the positioning tray.

7. An apparatus according to claim 6 wherein the plurality of color caps each has a step or bevel corresponding to a ledge formed in the positioning tray so that when the color caps are positioned in the positioning tray, the step or bevel is aligned with the ledge.

* * * * *